(12) United States Patent
Heida

(10) Patent No.: US 7,619,126 B2
(45) Date of Patent: Nov. 17, 2009

(54) METHOD FOR OBTAINING CRUDE 1,3-BUTADIENE FROM A $C_4$ FRACTION

(75) Inventor: Bernd Heida, Ellerstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 740 days.

(21) Appl. No.: 10/557,422

(22) PCT Filed: May 19, 2004

(86) PCT No.: PCT/EP2004/005407

§ 371 (c)(1),
(2), (4) Date: Nov. 18, 2005

(87) PCT Pub. No.: WO2004/103937

PCT Pub. Date: Dec. 2, 2004

(65) Prior Publication Data

US 2007/0039813 A1 Feb. 22, 2007

(30) Foreign Application Priority Data

May 20, 2003 (DE) .............................. 103 22 655

(51) Int. Cl.
- *C07C 7/08* (2006.01)
- *C07C 11/167* (2006.01)
- *B01D 3/40* (2006.01)
- *B01D 3/42* (2006.01)

(52) U.S. Cl. .............................. 585/615; 203/1; 203/23; 203/43; 203/58; 203/78; 203/99; 203/DIG. 19; 585/809; 585/810; 585/834; 585/865

(58) Field of Classification Search ..................... 203/1, 203/23, 43, 58, 78, 98, 99, DIG. 19; 585/615, 585/809, 810, 833, 834, 865
See application file for complete search history.

(56) References Cited

U.S. PATENT DOCUMENTS

| | | | |
|---|---|---|---|
| 3,620,930 A * | 11/1971 | Tschopp et al. | 203/87 |
| 4,162,198 A * | 7/1979 | Stockburger et al. | 203/23 |
| 6,846,966 B2 * | 1/2005 | Lumgair et al. | 585/639 |
| 7,132,038 B2 * | 11/2006 | Bohner et al. | 203/1 |

FOREIGN PATENT DOCUMENTS

| | | |
|---|---|---|
| DE | 27 24 365 | 11/1978 |
| DE | 101 02 168 | 6/2002 |
| DE | 101 05 660 | 8/2002 |

* cited by examiner

*Primary Examiner*—Virginia Manoharan
(74) *Attorney, Agent, or Firm*—Oblon, Spivak, McClelland, Maier & Neustadt, L.L.P.

(57) ABSTRACT

A process for recovering crude 1,3-butadiene from a $C_4$ fraction by extractive distillation using a selective solvent in a dividing wall column (TK) in which a dividing wall (T) is arranged in the longitudinal direction of the column to form a first subregion (A), a second subregion (B) and a lower common column region (C) and which is preceded by an extractive scrubbing column (K), wherein the operation of the dividing wall column (TK) is set by regulation of the energy input into the dividing wall column (TK) via a bottom vaporizer (V) and setting of the number of the theoretical plates in the lower common column region (C) so that a bottom stream (17) consisting of purified solvent is obtained from the dividing wall column (TK), is proposed.

15 Claims, 1 Drawing Sheet

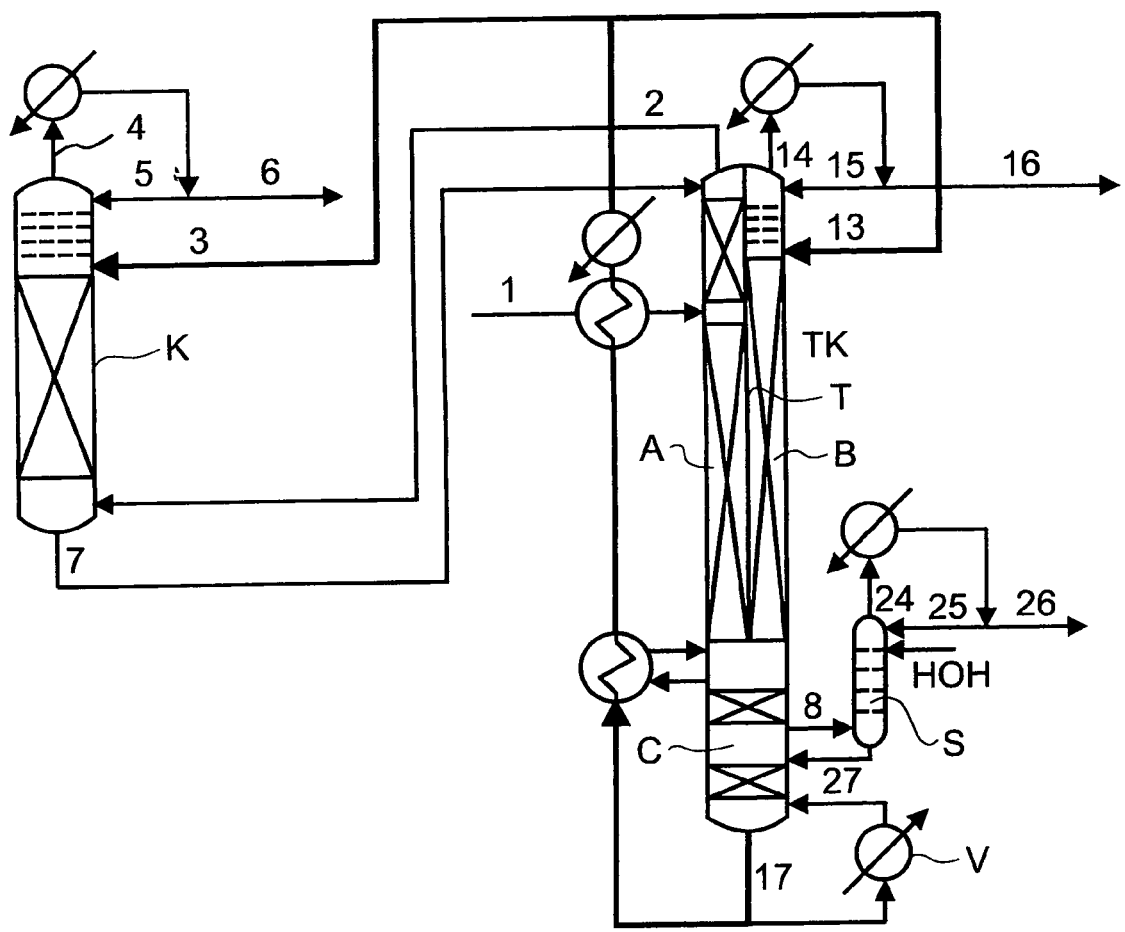

METHOD FOR OBTAINING CRUDE 1,3-BUTADIENE FROM A $C_4$ FRACTION

The present invention relates to a process for recovering crude 1,3-butadiene from a $C_4$ fraction by extractive distillation using a selective solvent.

The recovery of crude 1,3-butadiene from a $C_4$ fraction is a complicated distillation problem because of the small differences in the relative volatility of the components of the $C_4$ fraction. The fractionation is therefore carried out by means of an extractive distillation, i.e. a distillation with addition of an extractant which has a boiling point higher than that of the mixture to be fractionated and increases the differences in the relative volatility of the components to be separated. Use of suitable extractants enables the abovementioned $C_4$ fraction to be fractionated by means of extractive distillation to give a crude 1,3-butadiene fraction which is subsequently purified further in pure distillation columns together with a stream comprising the hydrocarbons which are less soluble than 1,3-butadiene, in particular butanes and butenes, and a stream comprising the hydrocarbons which are more readily soluble than 1,3-butadiene, in particular the butynes and possibly 1,2-butadiene.

For the purposes of the present invention, crude 1,3-butadiene is a hydrocarbon mixture which has been obtained from a $C_4$ fraction from which at least 90% by weight of the sum of butanes and butenes, preferably at least 96% by weight of the sum of butanes and butenes, particularly preferably at least 99% by weight of the sum of butanes and butenes, and at the same time at least 90% by weight of the $C_4$-acetylenes, preferably at least 96% by weight of the $C_4$-acetylenes, particularly preferably at least 99% by weight of the $C_4$-acetylenes, have been separated. Crude 1,3-butadiene frequently comprises a proportion of at least 80% by weight, preferably 90% by weight, particularly preferably 95% by weight, of 1,3-butadiene as product of value, with the balance being impurities.

On the other hand, the term pure 1,3-butadiene is used to refer to a hydrocarbon mixture comprising at least 99% by weight, preferably 99.5% by weight, particularly preferably 99.7% by weight, of 1,3-butadiene as product of value, with the balance being impurities.

DE 101 05 660.5 discloses a process having a simpler construction of the apparatuses compared to older processes: the fractionation of the $C_4$ fraction is carried out in a dividing wall column having a dividing wall which continues to the upper end of the dividing wall column and an extractive scrubbing column installed upstream of the dividing wall column.

The disclosure of the abovementioned DE 101 05 660.5 is hereby fully incorporated by reference into the present patent application.

In the process of DE 101 05 660.5, a partially degassed solvent stream is taken off from the bottom of the dividing wall column used for the extractive distillation. The term "partially degassed solvent" will be known to a person skilled in the art of extractive distillation for isolating 1,3-butadiene and refers to a selective solvent in which dissolved components from the $C_4$ fraction to be fractionated, namely the components which have the greatest affinity for the selective solvent, are still present. These components include, in particular, the $C_4$-acetylenes, especially ethylacetylene and vinylacetylene.

However, a merely partially degassed solvent stream cannot be recycled to the extractive distillation, since otherwise the acetylenes would accumulate and give rise to out-of-specification product. For this reason, the bottom stream taken off from the dividing wall column firstly has to be fed to a degasser column as is known, for example, from DE-A 27 24 365 which is operated at a pressure lower than that in the column from the bottom of which the partially degassed stream is taken off, before the bottom stream is recycled to the extractive distillation. In the degasser column, the partially degassed solvent stream is worked up to give a purified, i.e. completely degassed, solvent at the bottom and a gaseous hydrocarbonate stream at the top of the degasser column, and the latter stream is recirculated via a compressor to the lower region of the extractive distillation column.

In the present context, the term purified solvent or fully degassed solvent refers to a solvent which is depleted in components from the $C_4$ fraction to such an extent that it is suitable for use as selective solvent in the extractive distillation of a $C_4$ fraction so as to adhere to the prescribed specifications for crude 1,3-butadiene and raffinate 1. Key components are $C_4$-acetylene, in particular ethylacetylene and vinylacetylene.

It is an object of the present invention to provide a more economical process for recovering crude 1,3-butadiene from a $C_4$ fraction by extractive distillation and give a purified solvent directly from the bottom of the extractive distillation column.

The solution starts out from a process for recovering crude 1,3-butadiene from a $C_4$ fraction by extractive distillation using a selective solvent in a dividing wall column (TK) in which a dividing wall (T) is arranged in the longitudinal direction of the column to form a first subregion (A), a second subregion (B) and a lower common column region (C) and which is preceded by an extractive scrubbing column (K).

In the process of the present invention, the operation of the dividing wall column (TK) is set by regulation of the energy input into the dividing wall column (TK) via a bottom vaporizer (V) and setting of the number of the theoretical plates in the lower common column region (C) so that a bottom stream (17) consisting of purified solvent is obtained from the dividing wall column (TK).

It has surprisingly been found that purified solvent which can be recycled to the extractive distillation can be taken off directly from the bottom of the extractive distillation column without an additional degasser column being necessary for this purpose. To achieve this, it is possible and sufficient to set the energy input into the extractive distillation column via the bottom vaporizer and the number of theoretical plates in the lower common column region of the extractive distillation column configured as a dividing wall column so as to give operating conditions which allow purified solvent to be taken off out of the bottom of the extractive distillation column.

The $C_4$ fraction to be used as starting mixture in the present process is a mixture of hydrocarbons having predominantly four carbon atoms per molecule. $C_4$ fractions are obtained, for example, in the preparation of ethylene and/or propylene by thermal cracking of a petroleum fraction such as liquefied petroleum gas, light naphtha or gas oil. Furthermore, $C_4$ fractions are obtained in the catalytic dehydrogenation of n-butane and/or n-butene. $C_4$ fractions generally comprise butanes, n-butene, isobutene, 1,3-butadiene and small amounts of $C_3$- and $C_5$-hydrocarbons, and also butynes, in particular 1-butyne (ethylacetylene) and butenyne (vinylacetylene). The 1,3-butadiene content is generally from 10 to 80% by weight, preferably from 20 to 70% by weight, in particular from 30 to 60% by weight, while the content of vinylacetylene and ethylacetylene generally does not exceed 5% by weight.

For the present separation problem, namely the recovery of 1,3-butadiene from the $C_4$ fraction, possible extractants, i.e.

selective solvents, for the extractive distillation defined at the outset are substances or mixtures in general which have a boiling point higher than that of the mixture to be fractionated and have a greater affinity to conjugated double bonds and triple bonds than to simple double bonds or single bonds, preferably dipolar solvents, particularly preferably dipolar aprotic solvents. Substances which are noncorrosive or have little corrosivity are preferred so as to avoid corrosion of the apparatus.

Selective solvents which are suitable for the process of the present invention are, for example, butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amines (lactams) such as N-alkylpyrrolidones, in particular N-methylpyrrolidone. In general, use is made of N-alkyl-substituted lower aliphatic acid amides or N-alkyl-substituted cyclic acid amides. Particularly advantageous extractants are dimethylformamide, acetonitrile, furfural and, in particular, N-methylpyrrolidone.

It is also possible to use mixtures of these solvents with one another, for example of N-methylpyrrolidone with acetonitrile, mixtures of these solvents with cosolvents such as water and/or tert-butyl ethers, for example methyl tert-butyl ether, ethyl tert-butyl ether, propyl tert-butyl ether, n-butyl tert-butyl ether or isobutyl tert-butyl ether.

A particularly useful extractant is N-methylpyrrolidone, in the present text referred to as NMP for short, preferably in aqueous solution, in particular containing from 7 to 10% by weight of water, particularly preferably containing 8.3% by weight of water.

The extractive distillation is carried out in a dividing wall column in which a dividing wall is arranged in the longitudinal direction of the column to form a first subregion, a second subregion and a lower common column region and which is connected to an upstream extractive scrubbing column.

Dividing wall columns are, as is known, used for relatively complex separation tasks, in general for mixtures of at least three components which are each to be obtained in pure form. They have a dividing wall, i.e. generally a flat metal sheet aligned in the longitudinal direction of the column, which prevents transverse mixing of the liquid and vapor streams in subregions of the column.

For the purposes of the present invention, use is made of a dividing wall column having a particular configuration, whose dividing wall continues to the uppermost point of the column and thus allows mixing of liquid and vapor streams only in the lower common column region. The first and second subregions are separated from one another by the dividing wall.

The extractive scrubbing column is a countercurrent scrubbing column.

In a preferred way of carrying out the process,
the $C_4$ fraction is fed to the first subregion of the dividing wall column, preferably in its middle region,
the stream taken off at the top from the first subregion of the dividing wall column is fed to the extractive scrubbing column in its upper region,
a countercurrent extraction is carried out in the extractive scrubbing column by treatment with a first substream of the selective solvent in the upper region of the extractive scrubbing column,
the components of the $C_4$ fraction which are less soluble that 1,3-butadiene in the selective solvent are taken off at the top of the extractive scrubbing column,
the bottom stream from the extractive scrubbing column is recirculated to the upper region of the first subregion of the dividing wall column,
a second substream of the selective solvent is fed to the dividing wall column in the upper region of the second subregion,
the top product from the second subregion (B) of the dividing wall column is taken off as crude 1,3-butadiene and
a bottom stream consisting of purified solvent is taken off from the lower common column region of the dividing wall column and is recycled to the process.

It is thus preferred that the $C_4$ fraction to be fractionated is fed to the first subregion of the dividing wall column, particularly preferably in its middle region; the stream from the top of the first subregion of the dividing wall column is recirculated to the upstream extractive scrubbing column in its lower region, a countercurrent extraction is carried out in the extractive scrubbing column by treatment with a first substream of the selective solvent in the upper region of the extractive scrubbing column, the components of the $C_4$ fraction which are less soluble than 1,3-butadiene in the selective solvent are taken off at the top of the extractive scrubbing column, particularly preferably condensed in a condenser at the top of the extractive scrubbing column and partly returned as runback to the extractive scrubbing column while the remainder is taken off as a predominantly butane- and butene-containing by-product, often referred to as raffinate 1.

As a result of the recirculation of the stream from the bottom of the extractive scrubbing column, i.e. a stream comprising the selective solvent, 1,3-butadiene, butanes, butenes and the components of the $C_4$ fraction which are more soluble than 1,3-butadiene in the selective solvent, into the upper region of the first subregion of the dividing wall column and mass transfer between the stream and the $C_4$ fraction introduced in vapor form in the upper region of the first subregion of the dividing wall column, countercurrent extraction can take place with discharge of the components which are less soluble than 1,3-butadiene in the selective solvent at the top of the first subregion of the dividing wall column.

At the lower end of the dividing wall, a gaseous stream comprising 1,3-butadiene together with the components of the $C_4$ fraction which are more soluble than 1,3-butadiene in the selective solvent, in particular $C_4$-acetylenes, is obtained. These are scrubbed in countercurrent from the ascending gaseous stream by means of a second substream of the selective solvent which is introduced into the upper region of the second subregion of the dividing wall column. The gaseous product from the top of the second subregion of the dividing wall column is taken off and preferably condensed in a condenser at the top of the column, a substream of the condensed top stream is returned as runback to the subregion B of the dividing wall column and the remainder of the condensed top stream is taken off as crude 1,3-butadiene.

In the lower common column region, complete degassing of the solvent takes place, and a purified solvent is obtained at the bottom of the extractive distillation column.

In the determination of the energy input via the bottom vaporizer of the extractive distillation column which is necessary for this purpose, a process engineer will take into account the thermal stressability of the substance or substance mixture which is used as selective solvent in this specific case.

If the thermal stressability of the selective solvent permits, the temperature at the bottom of the extractive distillation column is advantageously set sufficiently high for a river of water still to be used for condensation at the top of the extractive distillation column.

However, if the thermal stressability of the selective solvent used in this specific case is not sufficient at the temperature which would be necessary to obtain a purified solvent at the bottom, the column has to be operated at a temperature at the bottom of the column which is still permissible for the selective solvent and, accordingly, a coolant which is more expensive than river water has to be used for cooling at the top of the column.

A particularly preferred selective solvent is, as indicated above, NMP, preferably in aqueous solution, in particular together with from 7 to 10% by weight of water, particularly preferably 8.3% by weight of water.

When NMP is used as selective solvent, the temperature at the bottom of the extractive distillation column is preferably set to a value in the range from 170 to 190° C., particularly preferably 180° C. The pressure at the top of the second subregion of the extractive distillation column configured as a dividing wall column is accordingly set to a value in the range from 1 to 10 bar absolute, preferably from 2 to 5 bar absolute, particularly preferably 3.5 bar absolute.

It is in principle not necessary to provide for the recovery of the by-product comprising butanes and butenes, namely raffinate 1, in a separate extractive scrubbing column installed upstream of the extractive distillation column. It is also possible to integrate the extractive scrubbing column into the first subregion of the dividing wall column used as extractive distillation column, as long as it is technically feasible and economically viable to increase the number of theoretical plates in the first subregion of the dividing wall column correspondingly given the specific boundary conditions for the process, in particular the composition of the $C_4$ fraction to be fractionated and the specification for raffinate 1.

The preferred process variants of the process of DE-A 101 05 660.5 described below can likewise be employed for the process of the present invention:

In a preferred process variant, the vapor stream at the lower end of the dividing wall of the dividing wall column is divided by means of suitable measures so that the substream conveyed to the first subregion of the dividing wall column is larger than the substream conveyed to the second subregion of the dividing wall column. Regulation of the division of the stream of vapor at the lower end of the dividing wall enables the necessary product specification of the crude 1,3-butadiene stream taken off at the top of the second subregion of the dividing wall column to be ensured in a simple and reliable manner.

Such unequal division of the stream vapor at the lower end of the dividing wall is particularly preferably achieved by the dividing wall being arranged noncentrally so that the second subregion is smaller than the first subregion of the dividing wall column.

The dividing wall is particularly preferably arranged noncentrally so that the cross-sectional ratio of the first subregion to the second subregion is in the range from 8:1 to 1.5:1, in particular 2.3:1.

As an alternative to or in addition to the noncentral arrangement of the dividing wall, the stream of vapor at the lower end of the dividing wall can be divided in the desired ratio between the two subregions of the dividing wall column by means of further measures, for example flaps or guide plates.

A further additional or alternative measure for division of the stream of vapor at the lower end of the dividing wall is setting of the heat removal power of the condenser at the top of the second subregion of the dividing wall column.

In a preferred process variant, the pressures at the upper end of the two subregions of the dividing wall column can each be regulated separately. This enables the necessary product specification of the crude 1,3-butadiene to be ensured.

The pressures at the top of the two subregions of the dividing wall column are preferably each set by means of a split-range control. The term split-range control refers, in a well-known manner, to an arrangement in which the outlet of the pressure regulator is connected simultaneously to the inert gas line and the venting line. The valve setting range of the pressure regulator is divided so that only one valve is actuated at one time, i.e. either inert gas flows in or venting occurs. This enables the amount of inert gas and the product losses associated with the waste air stream to be minimized.

In addition to or as an alternative to split-range control, it is possible to regulate each of the pressures at the top of the two subregions of the dividing wall column by means of the heat removal power of the condensers at the top of the second subregion of the dividing wall column and at the top of the extractive scrubbing column.

In a preferred process variant, the pressure at the top of the second subregion of the dividing wall column is set so as to be greater than that in the first region of the dividing wall column, in particular by 1-100 mbar, particularly preferably by 1-30 mbar. This measure makes it possible to dispense with a fixed, welded-in or expensively sealed dividing wall and to use a cheaper removable dividing wall. The pressure drop from the second to the first subregion of the dividing wall column allows liquid or gaseous leakage flows to occur only in this direction, so that they are not critical for the purity of the desired crude 1,3-butadiene taken off at the top of the second subregion.

The heat contents of the bottom stream of purified solvent can advantageously be utilized in the process itself by means of heat integration, in particular by taking off liquid or a substream of the liquid from the lower common column region of the dividing wall column at one or more points, heating and/or vaporizing this liquid by indirect heat exchange with the hot bottom stream from the extractive distillation column and returning it to the lower common column region.

The theoretical plate from which the liquid or the substream of liquid is taken off is preferably selected so that the total energy requirement for the extractive distillation column is minimized.

In addition or as an alternative, the heat content of the bottom stream of purified solvent can also be utilized for indirect heat exchange with the $C_4$ fraction to be fed into the extractive distillation column.

To remove the $C_4$-acetylenes, in particular ethylacetylene and vinylacetylene, from the process, preference is given to taking off a sidestream from the lower common column region of the dividing wall column, passing it to a scrubbing column in which the sidestream is scrubbed with water, taking off a top stream from the scrubbing column and condensing this partially or completely, preferably partially, discharging parts of the condensate and returning the remainder as runback to the scrubbing column and taking off the bottom stream from the scrubbing column and feeding it back into the lower common column region.

The invention thus provides a process for recovering crude 1,3-butadiene from a $C_4$ fraction by extractive distillation which, compared to known processes, makes it possible to recover purified solvent, which is preferably recycled to the process, directly from the bottom of the extractive distillation column. As a result of the saving of the degasser column which has hitherto been required for this purpose and the associated equipment, in particular heat exchangers and pumps but especially the compressor for compressing the hydrocarbon stream to be recirculated to the extractive distillation column, the capital costs are lower than for known processes. The ability to dispense with the compressor which is by far the greatest power consumer in the process of the prior art is particularly advantageous. As a result of the compressor being dispensed with, the consumption of electrical energy in the process of the present invention is approximately halved compared to the process of the prior art.

The invention is illustrated below with the aid of a drawing:

FIG. 1 shows a flow diagram of an apparatus according to the invention.

In a dividing wall column TK having a dividing wall T which is arranged in the longitudinal direction of the column and divides the dividing wall column into a first subregion A, a second subregion B and a lower common column region C, a $C_4$ fraction 1 is fed into the first subregion A. For example, the second subregion B has 40 theoretical plates and the lower common column region C has 10 theoretical plates. The stream 2 from the top of the subregion A is conveyed to the lower region of the upstream extractive scrubbing column K having, for example, 19 theoretical plates. A first solvent substream 3 is introduced into the upper region of the extractive scrubbing column K, so that countercurrent extraction takes place and gives a bottom stream 7 which is returned to the upper region of the subregion A of the dividing wall column TK and a top stream 4 which is condensed in a condenser at the top of the extractive scrubbing column K, with a substream of the condensate being returned as stream 5 to the extractive scrubbing column K and the remainder of the condensate being taken off as stream 6.

A second solvent substream 13 is introduced into the second subregion B of the dividing wall column TK. A top stream 14 has taken off from the second subregion B and condensed, a substream 15 of the condensed top stream 14 is returned as runback to the second subregion B of the dividing wall column and the remainder of the condensed top stream 14 is taken off as crude 1,3-butadiene (stream 16).

In the preferred embodiment as shown in the figure, a side stream 8 is taken off from the lower common column region C, and fed to a scrubbing column S and is scrubbed with water (stream HOH) in the scrubbing column S. A top stream 24 is taken off from the scrubbing column S, condensed in a condenser, part of the condensate (stream 25) is returned as runback to the scrubbing column S and the remainder is discharged as stream 26 comprising the $C_4$-acetylenes. A stream 27 is taken off from the bottom of the scrubbing column S and is fed back into the lower common column region C of the dividing wall TK. The bottom vaporizer of the dividing wall column TK is denoted by V. The bottom stream 17 from the dividing wall column TK, which consists of purified solvent, for example NMP having a water content of 8.3% by weight, is utilized for heat integration with a liquid stream taken off from the lower common column region C of the dividing wall column TK and is, after being heated by the stream 17, fed back into the lower common column region. In addition, it is possible, as shown by way of example in the figure, for the heat content of the bottom stream 17 to be used advantageously for preheating of the $C_4$ fraction (stream 1) fed to the dividing wall column TK.

I claim:

1. A process for recovering crude 1,3-butadiene from a $C_4$ fraction, comprising:
   extractively distilling the $C_4$ fraction using a selective solvent in a dividing wall column in which a dividing wall is arranged in the longitudinal direction of the column to form a first subregion, a second subregion and a lower common column region, a topstream from the first subregion being conveyed to an upstream extractive scrubbing column,
   wherein the operation of the dividing wall column is set by regulating the energy input into the dividing wall column via a bottom vaporizer and setting of the number of the theoretical plates in the lower common column region so that a bottom stream of purified solvent is obtained from the dividing wall column.

2. A process as claimed in claim 1, wherein liquid or a substream of liquid is taken off from the lower common column region at one or more points, heated and/or vaporized by indirect heat exchange with the bottom stream from the dividing wall column and fed back into the lower common column region of the dividing wall column.

3. A process as claimed in claim 2, wherein the liquid or the substream of the liquid is taken off from the lower common column region of the dividing wall column at a theoretical plate which is selected so that the energy requirement for the dividing wall column is minimized.

4. A process as claimed in claim 1, wherein part of the energy of the bottom stream from the dividing wall column is utilized for indirect heat exchange with the $C_4$ fraction to be fractionated which is fed to the dividing wall column.

5. A process as claimed in claim 1, wherein the extractive scrubbing column is structurally integrated into the first subregion of the dividing wall column by making the number of theoretical plates in the first subregion of the dividing wall column correspondingly larger.

6. A process as claimed in claim 1, wherein a side stream is taken off from the lower common column region of the dividing wall column, the side stream is fed to a scrubbing column in which a water scrub is carried out, a top stream is taken off from the scrubbing column, condensed completely in a condenser at the top of the scrubbing column, part of the condensate is returned as runback to the scrubbing column and the remainder is discharged as a stream comprising $C_4$-acetylenes and the bottom stream from the scrubbing column is recirculated to the lower common column region of the dividing wall column.

7. The process as claimed in claim 6, wherein the top stream taken off from the scrubbing column is condensed partially in the condenser at the top of the column.

8. A process as claimed in claim 1, further comprising:
   feeding the $C_4$ fraction to the first subregion of the dividing wall column,
   feeding the stream taken off at the top from the first subregion of the dividing wall column to the extractive scrubbing column in its upper region,
   carrying out a countercurrent extraction in the extractive scrubbing column by treating with a first substream of the selective solvent in the upper region of the extractive scrubbing column,
   taking off the components of the $C_4$ fraction which are less soluble than 1,3-butadiene in the selective solvent at the top of the extractive scrubbing column,
   recirculating the bottom stream from the extractive scrubbing column to the upper region of the first subregion of the dividing wall column,
   feeding a second substream of the selective solvent to the dividing wall column in the upper region of the second subregion,
   taking off the top product from the second subregion of the dividing wall column as crude 1,3-butadiene and taking off a bottom stream of purified solvent from the lower common column region of the dividing wall column and recycling the purified solvent to the process.

9. The process as claimed in claim 8, wherein the $C_4$ fraction is fed to the first subregion of the dividing wall column in its middle region.

10. The process as claimed in claim 1, wherein the selective solvent used is N-methylpyrrolidone.

11. The process as claimed in claim 10, wherein the selective solvent used is N-methylpyrrolidone in aqueous solution.

12. The process as claimed in claim 11, wherein the aqueous solution of N-methylpyrrolidone has a water content of from 7 to 10% by weight.

13. The process as claimed in claim 12, wherein the aqueous solution of N-methylpyrrolidone has a water content of 8.3% by weight.

14. The process as claimed in claim 1, wherein the temperature in the bottom of the dividing wall column is regulated in the range from 170 to 190° C., and the pressure at the top of the second subregion of the dividing wall column is regulated in the range from 1 to 10 bar absolute.

15. The process as claimed in claim 14, wherein the temperature in the bottom of the dividing wall column is regulated at 180° C., and the pressure at the top of the second subregion of the dividing wall column is regulated at 3.5 bar absolute.

* * * * *